US009820858B2

(12) United States Patent
Harris et al.

(10) Patent No.: US 9,820,858 B2
(45) Date of Patent: Nov. 21, 2017

(54) KNEE IMPLANTS AND INSTRUMENTS

(71) Applicant: Modal Manufacturing, LLC, North Palm Beach, FL (US)

(72) Inventors: Thomas Bradley Harris, Palm Beach Gardens, FL (US); Andrew Meredith Rynearson, Winter Springs, FL (US)

(73) Assignee: Modal Manufacturing, LLC, North Palm Beach, FL (US)

( * ) Notice: Subject to any disclaimer, the term of this patent is extended or adjusted under 35 U.S.C. 154(b) by 0 days.

(21) Appl. No.: 14/665,511

(22) Filed: Mar. 23, 2015

(65) Prior Publication Data

US 2016/0278929 A1   Sep. 29, 2016

(51) Int. Cl.
*A61F 2/38* (2006.01)
*A61B 17/15* (2006.01)
*A61F 2/30* (2006.01)

(52) U.S. Cl.
CPC ............ *A61F 2/389* (2013.01); *A61B 17/155* (2013.01); *A61F 2002/30884* (2013.01); *A61F 2220/0008* (2013.01)

(58) Field of Classification Search
CPC .. A61F 2/389; A61F 2002/30884; A61F 2/38; A61F 2/3868; A61B 17/157; A61B 17/1675
See application file for complete search history.

(56) References Cited

U.S. PATENT DOCUMENTS

| | | | | |
|---|---|---|---|---|
| 5,129,909 A * | 7/1992 | Sutherland | ............ | A61B 17/155 606/53 |
| 5,364,401 A * | 11/1994 | Ferrante | ............... | A61B 17/155 606/102 |
| 5,702,461 A * | 12/1997 | Pappas | .................... | A61F 2/389 606/213 |
| 5,709,689 A * | 1/1998 | Ferrante | ............... | A61B 17/155 606/80 |
| 5,716,361 A * | 2/1998 | Masini | ................. | A61B 17/154 606/82 |
| 5,824,103 A * | 10/1998 | Williams | ................. | A61F 2/389 623/20.32 |
| 5,911,723 A * | 6/1999 | Ashby | .................. | A61B 17/154 606/88 |
| 6,258,095 B1 * | 7/2001 | Lombardo | ............ | A61B 17/154 606/87 |
| 6,355,045 B1 * | 3/2002 | Gundlapalli | ....... | A61B 17/1764 606/86 R |
| 7,104,997 B2 * | 9/2006 | Lionberger | ........... | A61B 17/155 606/88 |
| 7,695,519 B2 * | 4/2010 | Collazo | .................... | A61F 2/389 623/20.15 |

(Continued)

Primary Examiner — Alvin Stewart
(74) Attorney, Agent, or Firm — McHale & Slavin, P.A.

(57) ABSTRACT

A tibial tray component includes a tibial tray portion with a post portion protruding from a bone-contacting side of the tibial tray portion. The tibial tray portion may include ribs extending along the bone-facing side in areas of high stress during the gait cycle. The post portion may include at least one fin projecting outwardly from the post portion and extending along a portion of the length of the post portion. A cut block assembly includes a cut block and at least one pin. The cut block may include several mounting locations for the pin. The pin may include an anti-rotation portion and a tapered free end.

12 Claims, 17 Drawing Sheets

(56) References Cited

U.S. PATENT DOCUMENTS

| | | | |
|---|---|---|---|
| D651,316 S * | 12/2011 | May | A61F 17/1764 D24/140 |
| 8,323,288 B2 * | 12/2012 | Zajac | A61B 17/155 606/86 R |
| D694,884 S * | 12/2013 | Mooradian | A61B 17/1764 D24/140 |
| 8,986,390 B2 * | 3/2015 | Wogoman | A61F 2/4684 623/20.15 |
| 2005/0075640 A1 * | 4/2005 | Collazo | A61B 17/1764 606/86 R |
| 2005/0209605 A1 * | 9/2005 | Grimm | A61B 17/154 606/96 |
| 2006/0157543 A1 * | 7/2006 | Abkowitz | A61F 2/30767 228/233.2 |
| 2006/0184176 A1 * | 8/2006 | Straszheim-Morley | A61B 17/1764 606/88 |
| 2006/0241634 A1 * | 10/2006 | Tuttle | A61B 17/1675 606/86 R |
| 2006/0265079 A1 * | 11/2006 | D'Alessio, II | A61F 2/30721 623/20.15 |
| 2007/0010890 A1 * | 1/2007 | Collazo | A61F 2/389 623/20.15 |
| 2007/0055268 A1 * | 3/2007 | Utz | A61B 17/155 606/87 |
| 2007/0118138 A1 * | 5/2007 | Seo | A61B 17/154 606/87 |
| 2007/0173946 A1 * | 7/2007 | Bonutti | A61B 17/025 623/20.14 |
| 2007/0203582 A1 * | 8/2007 | Campbell | A61F 2/389 623/20.34 |
| 2007/0226986 A1 * | 10/2007 | Park | A61B 17/155 29/592 |
| 2007/0233137 A1 * | 10/2007 | Seo | A61B 17/157 606/87 |
| 2007/0233140 A1 * | 10/2007 | Metzger | A61B 17/155 606/88 |
| 2007/0255412 A1 * | 11/2007 | Hajaj | A61F 2/38 623/17.11 |
| 2007/0282451 A1 * | 12/2007 | Metzger | A61B 17/1675 623/20.28 |
| 2007/0288030 A1 * | 12/2007 | Metzger | A61B 17/154 606/87 |
| 2008/0015602 A1 * | 1/2008 | Axelson | A61B 17/155 606/87 |
| 2008/0183177 A1 * | 7/2008 | Fox | A61B 17/1604 606/88 |
| 2009/0084491 A1 * | 4/2009 | Uthgenannt | A61F 2/389 156/153 |
| 2009/0125114 A1 * | 5/2009 | May | A61B 17/1764 623/20.14 |
| 2009/0265011 A1 * | 10/2009 | Mandell | A61B 17/155 623/20.15 |
| 2010/0298947 A1 * | 11/2010 | Unger | A61F 2/38 623/20.32 |
| 2011/0082559 A1 * | 4/2011 | Hartdegen | A61F 2/389 623/20.32 |
| 2011/0190898 A1 * | 8/2011 | Lenz | A61F 2/38 623/20.32 |
| 2012/0245589 A1 * | 9/2012 | Fisher | A61B 17/157 606/87 |
| 2013/0006376 A1 * | 1/2013 | Wogoman | A61F 2/389 623/20.32 |
| 2013/0006377 A1 * | 1/2013 | Waite, II | A61B 17/1764 623/20.32 |
| 2013/0218284 A1 * | 8/2013 | Eickmann | A61F 2/389 623/20.34 |
| 2013/0296865 A1 * | 11/2013 | Aram | A61B 17/1764 606/80 |
| 2013/0325014 A1 * | 12/2013 | Sordelet | A61B 17/155 606/82 |
| 2014/0277539 A1 * | 9/2014 | Cook | A61F 2/30 623/20.32 |
| 2014/0277541 A1 * | 9/2014 | Wyss | A61F 2/389 623/20.32 |
| 2014/0343558 A1 * | 11/2014 | Porzel | B22F 3/24 606/88 |
| 2014/0364857 A1 * | 12/2014 | Bojarski | A61B 17/155 606/89 |
| 2015/0025645 A1 * | 1/2015 | Cho | A61F 2/3886 623/20.29 |
| 2015/0134070 A1 * | 5/2015 | Waite, II | A61B 17/1764 623/20.32 |
| 2015/0190236 A1 * | 7/2015 | McMinn | A61F 2/3859 623/20.27 |
| 2015/0202048 A1 * | 7/2015 | Roisin | A61F 2/389 623/20.32 |
| 2015/0238316 A1 * | 8/2015 | Lin | A61F 2/4684 623/20.15 |
| 2015/0313727 A1 * | 11/2015 | Waite, II | A61B 17/1675 623/20.32 |

\* cited by examiner

KNEE IMPLANTS AND INSTRUMENTS

CROSS REFERENCE TO RELATED APPLICATIONS

Not Applicable

STATEMENT REGARDING FEDERALLY SPONSORED RESEARCH OR DEVELOPMENT

Not Applicable

FIELD OF THE INVENTION

The present disclosure relates to orthopedic implants and instruments.

BACKGROUND

This disclosure is presented in the context of implants and instruments for knee arthroplasty, but it will be appreciated that this technology may be applicable in other areas of the body where similar implants and surgical procedures. For example, the present technology may be applied in implants and instruments for other joints of the body.

A knee arthroplasty system may include a tibial tray component for mounting to a prepared proximal tibia. The tibial tray component may be unicondylar, replacing one condyle of the proximal tibia, or bicondylar, replacing two condyles. The knee arthroplasty system may also include a femoral component for mounting to a prepared distal femur and interacting with the tibial tray component. The knee arthroplasty system may also include an articular insert component for mounting between the tibial tray component and the femoral component, and for articular motion with at least one of the tibial tray component and the femoral component. The femoral component and articular insert component, if present, may be unicondylar or bicondylar. Frequently, unicondylar components are used together, or bicondylar components are used together, however mixed use is contemplated. A patellar component may also be provided in some knee arthroplasty systems. A knee arthroplasty system may also include surgical instruments for use in preparing the tibia, femur, and/or patella.

SUMMARY OF THE INVENTION

Disclosed is a tibial tray component that includes a tibial tray portion with a post portion protruding from a bone-contacting side of the tibial tray portion. The tibial tray portion may include ribs extending along the bone-facing side in areas of high stress during the gait cycle. The post portion may include at least one fin projecting outwardly from the post portion and extending along a portion of the length of the post portion. A cut block assembly includes a cut block and at least one pin. The cut block may include several mounting locations for the pin. The pin may include an anti-rotation portion and a tapered free end.

An objective of the invention is to disclose a system comprising a tibial tray component comprising a tibial tray portion and a cut block assembly comprising a cut block and at least one pin coupled to the cut block, wherein the pin comprises an anti-rotation portion.

Another objective of the invention is to disclose a system comprising a tibial tray component comprising a tibial tray portion and a post portion, wherein the post portion protrudes from a bone-facing side of the tibial tray portion, wherein the post portion comprises a longitudinal fin which protrudes from the post portion, wherein the fin projects anteriorly when the tibial tray component is operatively mounted to a prepared proximal tibia.

Still another objective of the invention is to disclose a system comprising a tibial tray component comprising a tibial tray portion, wherein the tibial tray portion comprises a bone-facing side, wherein the bone-facing side comprises at least one protruding rib extending in an area of high service stress when the tibial tray component is operatively mounted to a prepared proximal tibia.

Yet still another objective of the invention is to disclose a system comprising a cut block assembly comprising a cut block and at least one pin coupled to the cut block, wherein the pin comprises a tapered free end.

Another objective of the invention is to disclose a system comprising a cut block assembly comprising a cut block and at least one pin coupled to the cut block, wherein the cut block comprises a plurality of mounting locations for coupling the pin to the cut block.

Other objectives and further advantages and benefits associated with this invention will be apparent to those skilled in the art from the description, examples and claims which follow.

DETAILED DESCRIPTION OF THE INVENTION

Figure 1:
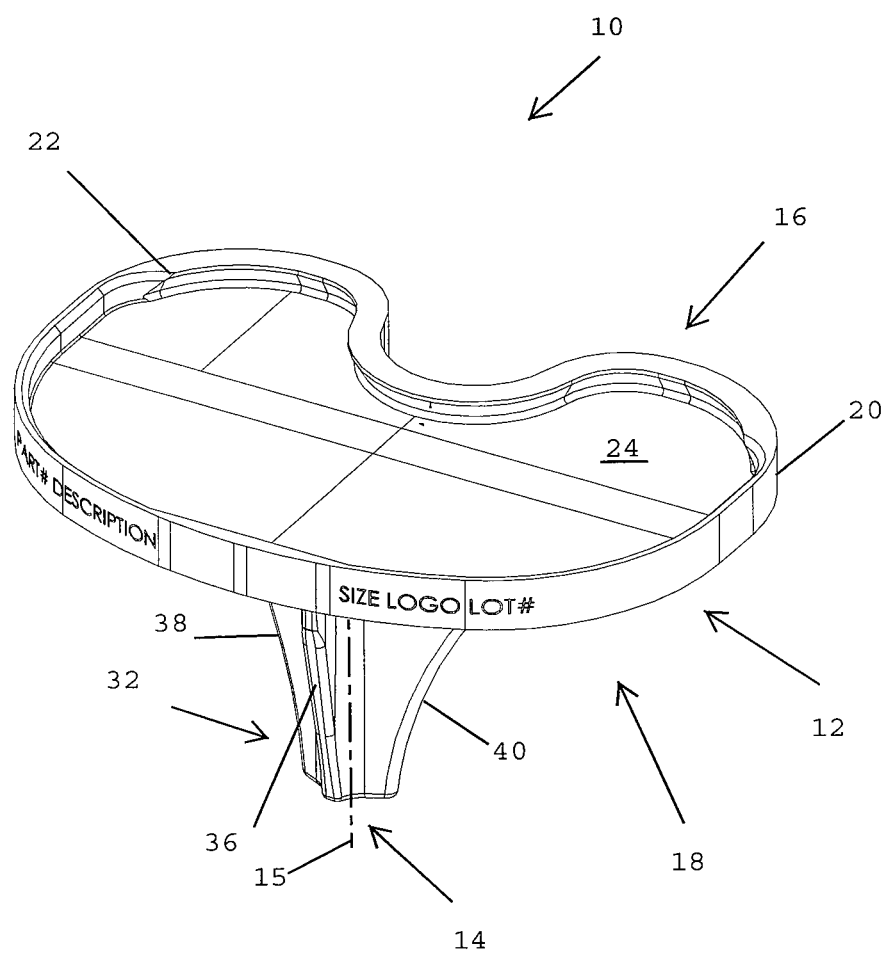
FIG. 1 is an anterior superior isometric view of a tibial tray component.

While examples of the present technology have been shown and described in detail below, it will be clear to the person skilled in the art that variations, changes and modifications may be made without departing from its scope. As such, that which is set forth in the following description and accompanying drawings is offered by way of illustration only and not as a limitation. The actual scope of the invention is intended to be defined by the following claims, along with the full range of equivalents to which such claims are entitled.

In the following Detailed Description, various features are grouped together in several examples for the purpose of streamlining the disclosure. This method of disclosure is not to be interpreted as reflecting an intention that examples of the technology require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example.

Identical reference numerals do not necessarily indicate an identical structure. Rather, the same reference numeral may be used to indicate a similar feature or a feature with similar functionality. Not every feature of each example is labeled in every figure in which that example appears, in order to keep the figures clear. Similar reference numbers (e.g., those that are identical except for the first numeral) may be used to indicate similar features in different examples.

Standard medical planes of reference and descriptive terminology are employed in this specification. A sagittal plane divides a body into right and left portions. A mid-sagittal plane divides the body into bilaterally symmetric right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. These descriptive terms may be applied to an animate or inanimate body.

Referring to FIGS. 1-6, a bicondylartibial tray component 10 may include a tray portion 12 and a post portion 14. The tray portion 12 may include a superior side 16, an inferior side 18, and a peripheral wall 20 extending between the superior side 16 and the inferior side 18.

The superior side 16 may be referred to as a joint-facing side since it faces toward the knee joint when the tibial tray component 10 is operatively mounted to a prepared proximal tibia. The superior side 16 may include an articular surface for articulation with a natural or artificial distal femoral condyle or condyles. However, in the example shown, the superior side 16 is adapted for engagement with an articular insert component (not shown) and thus lacks an articular surface. The superior side 16 includes a locking feature 22 and a superior surface 24. The locking feature in this example includes a posterior portion, seen in FIG. 1, and/or an anterior portion, seen in FIG. 3. The superior surface 24 may be complementary to a corresponding inferior surface of an articular insert component. In this example, the superior surface 24 may be planar, concave, or convex.

Figure 2:
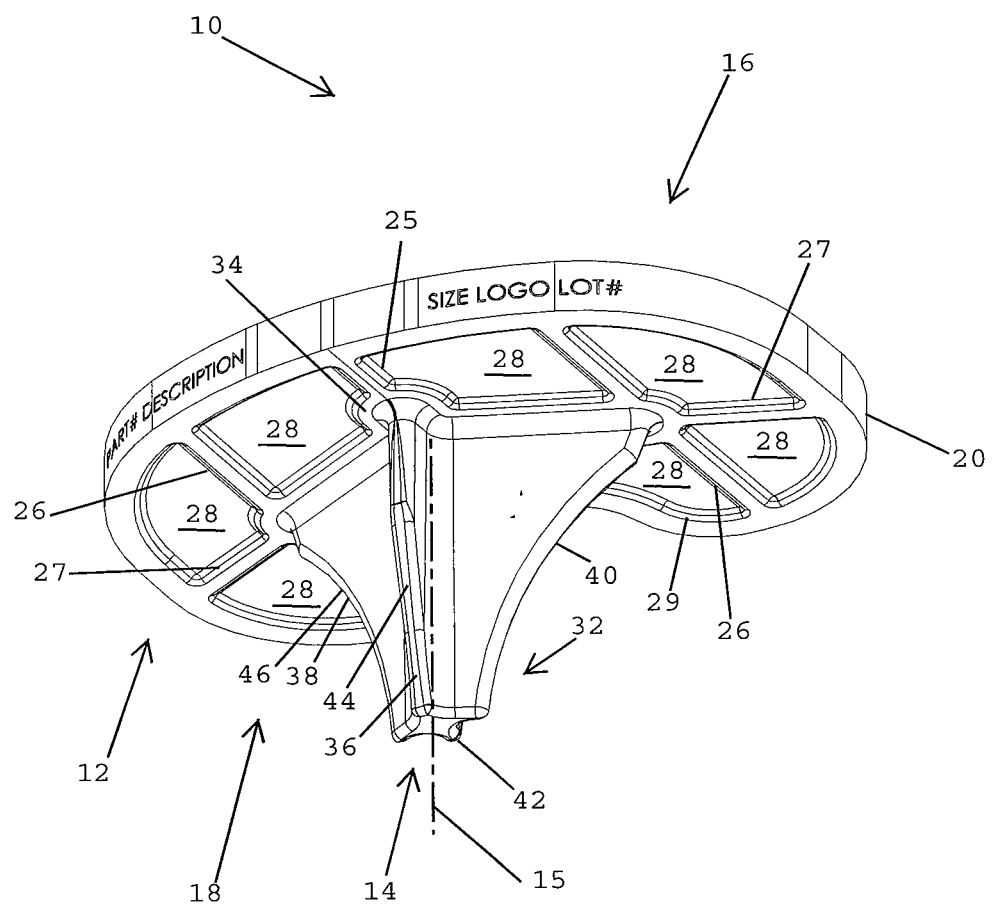
FIG. 2 is an anterior inferior isometric view of the tibial tray component of FIG. 1.
Figure 3:
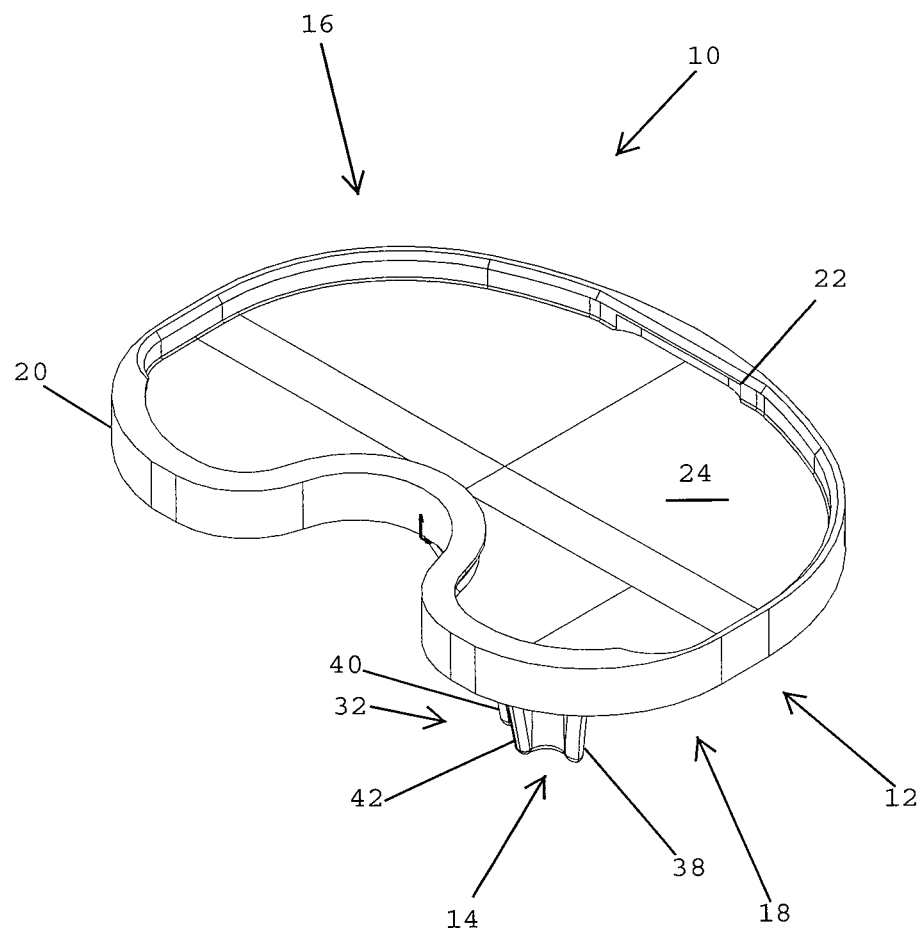
FIG. 3 is a posterior superior isometric view of the tibial tray component of FIG. 1.
Figure 4:
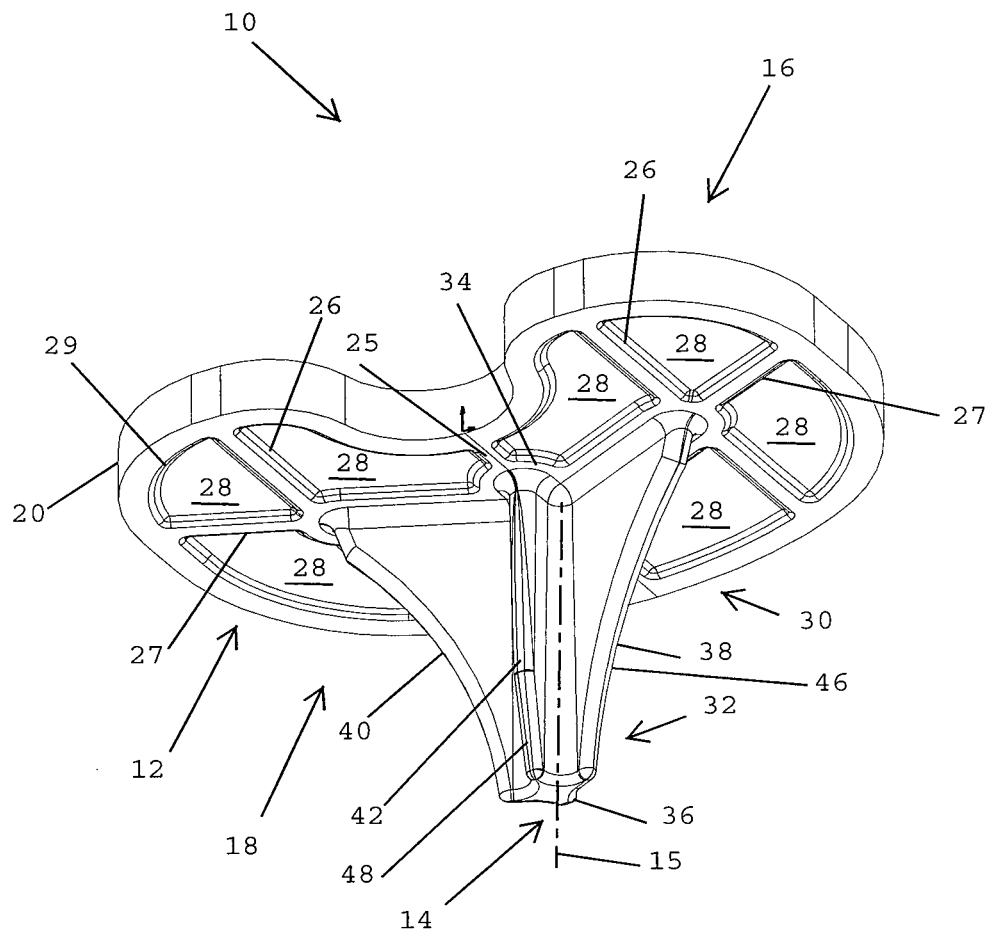
FIG. 4 is a posterior inferior isometric view of the tibial tray component of FIG. 1.
Figure 5:
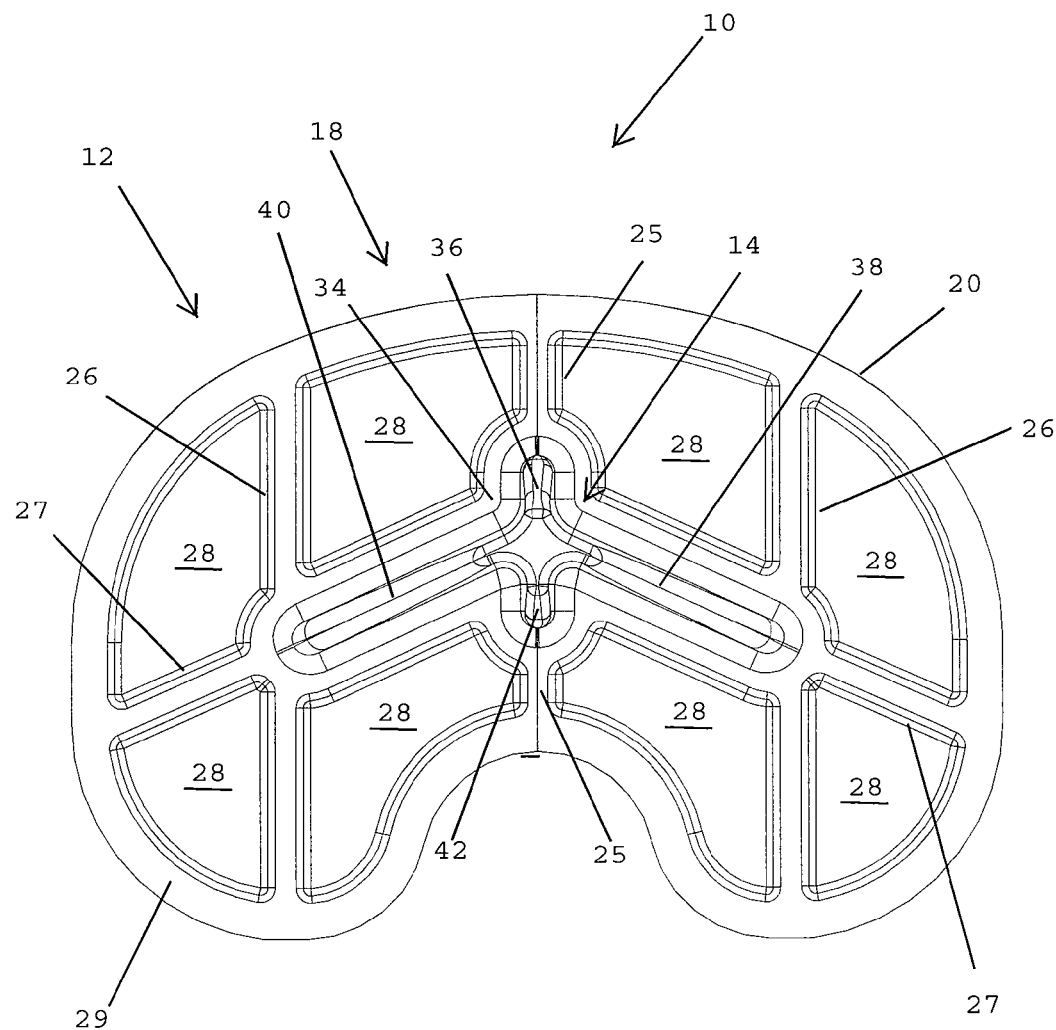
FIG. 5 is an inferior view of the tibial tray component of FIG. 1.

The inferior side 18 may be referred to as a bone-facing side since it faces toward the tibia when the tibial tray component 10 is operatively mounted to a prepared proximal tibia. The inferior side 18 may include adaptations, features, and/or coatings to enhance short-term and/or long-term fixation directly to bone, or indirectly through a medium such as bone cement. Referring to FIGS. 2, 4, and 5, the inferior side 18 may include one or more ribs 26 and an inferior surface 28. The ribs 26 may be located anywhere on the inferior side 18 of the tibial tray portion 12. More specifically, the ribs 26 may be located in areas that experience the highest service stresses and/or service forces during at least a portion of a gait cycle (a single gait cycle begins with ground contact by a selected foot, and ends with the next ground contact by the selected foot). These areas may, for example, extend across the tibial tray portion 12 generally from anterior to posterior, coinciding with the direction of knee flexion and extension motion. These areas may also include an arcuate quality coinciding with the direction of relative axial rotation of the tibia relative to the femur. Forces and/or stresses in the tibial tray component 10 may be due to loading by a natural or artificial distal femoral condyle or condyles, and may be transferred directly due to direct articulation, or indirectly through an intermediate articular insert component. It will be appreciated that the force and/or stress distribution in any given tibial tray component 10 will depend upon many factors, such as the nominal or basic design of the implant component(s), their tolerances and materials, and the geometry, fit, and compliance of surrounding bony structures. In the present example, an anterior-posterior rib 26' extends across each condyle of the tibial tray portion 12. A central anterior-posterior rib 25 extends across the tibial tray portion 12 and intersects the post portion 14. Oblique ribs 27 extend postero-laterally from the post portion 14. A peripheral rib 29 extends around the tibial tray portion 12, congruent with the peripheral wall 20. In other examples, the ribs may extend medio-laterally, oblique antero-laterally, radially, or annularly. The ribs 26 may be angled, bent, curved, wavy, or otherwise depart from straight. The inferior surface 28 may extend across the inferior side except where the ribs 26 are located. The inferior surface 28 may therefore appear to be segmental, discontinuous, or interrupted; however, the various portions of the inferior surface 28 may form a congruent continuous planar, convex, or concave surface. The interior corners formed between the ribs 26 and the inferior surface 28 may be radiused or filleted to reduce stress concentrations; exterior corners may also be radiused or otherwise blunted.

The peripheral wall 20 may mimic, duplicate, or approximate a natural profile of a proximal tibia from a superior view. While the peripheral wall 20 is shown extending intact around the perimeter of the tibial tray portion 12, one or more interruptions, apertures, passageways, protrusions, or other discontinuities may be present. As one example, the peripheral wall 20 may include an indentation for registration with a corresponding surgical instrument.

The post portion 14 extends from the inferior side 18. A proximal portion 30 of the post portion 14 couples or mounts to the inferior side 18. The proximal portion 30 of the post portion 14 may be located so as to intersect one or more ribs 26. In the example shown, the proximal portion 30 intersects the central anterior-posterior rib 25 and the oblique ribs 27, as shown in FIG. 5. A platform 34 may be included at the intersection of the proximal portion 30 and the ribs 26. A distal portion 32 of the post portion 14 may terminate at a free end located a distance from the tibial tray portion 12.

The post portion 14 may include one or more fins 36 which may project radially from a longitudinal axis 15 of the post portion 14. The fin 36 limits rotation of the tibial tray component 10 about the axis 15 when the tibial tray component 10 is operatively mounted to a prepared proximal tibia. The fin 36 also adds structural support to the tibial tray component, particularly in the juncture between the inferior side 18 and the post portion 14. In the example shown, there are four fins 36, 38, 40, 42 arranged around the post portion 14. More specifically, there is an anterior fin 36, a right fin 38, a left fin 40, and a posterior fin 42. Four fins may provide greater rotational stability and strength than one fin would provide. However, any number of fins may be present. The height of each fin from the post portion may be the same as, or different from, other fins around the post portion. The thickness of each fin may be the same as, or different from, other fins around the post portion. The length of each fin may be the same as, or different from, other fins around the post portion. The height and thickness of a fin may be constant or variable over the length of that fin.

Figure 6:
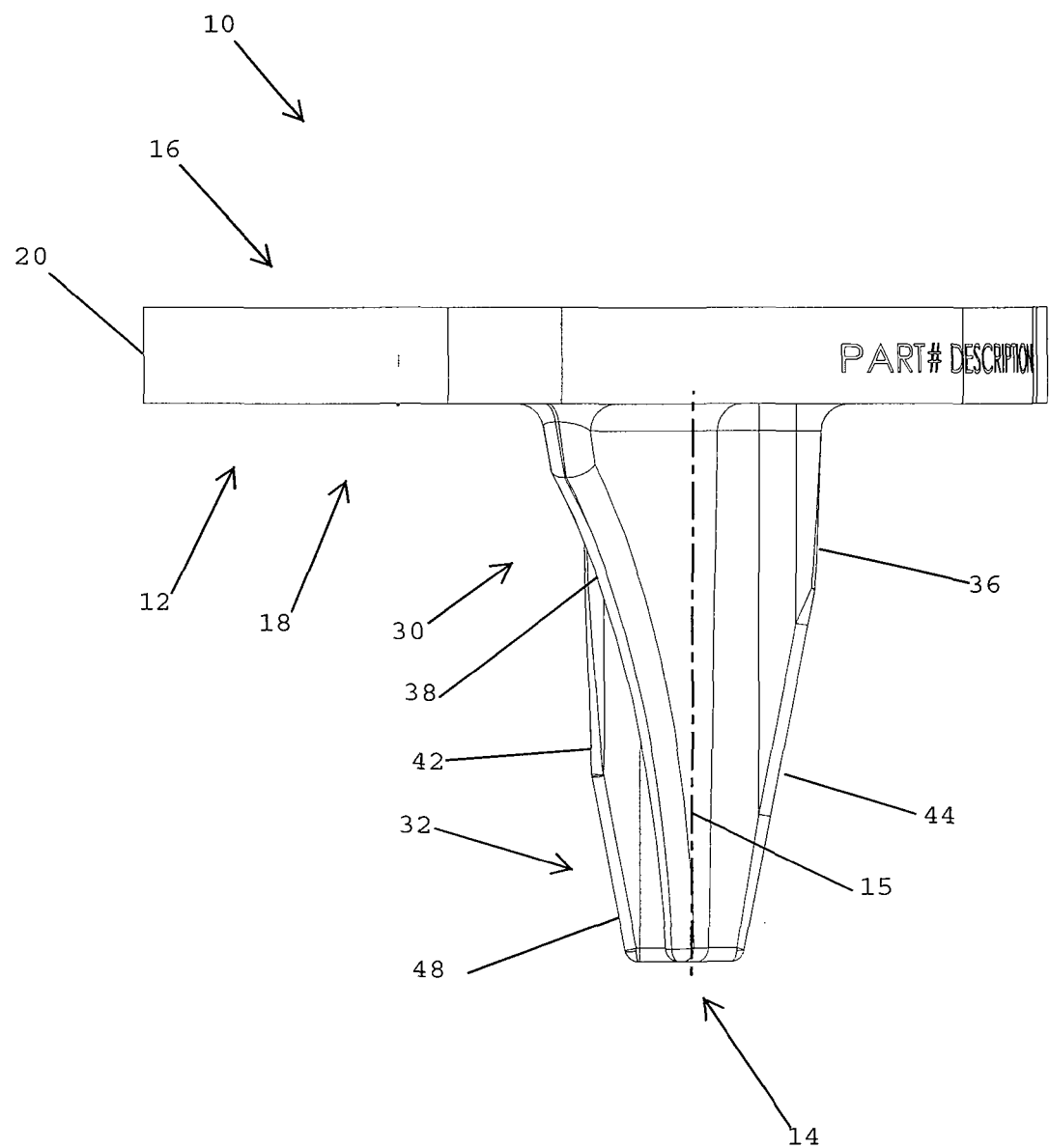
FIG. 6 is a side view of the tibial tray component of FIG. 1.
Figure 7:
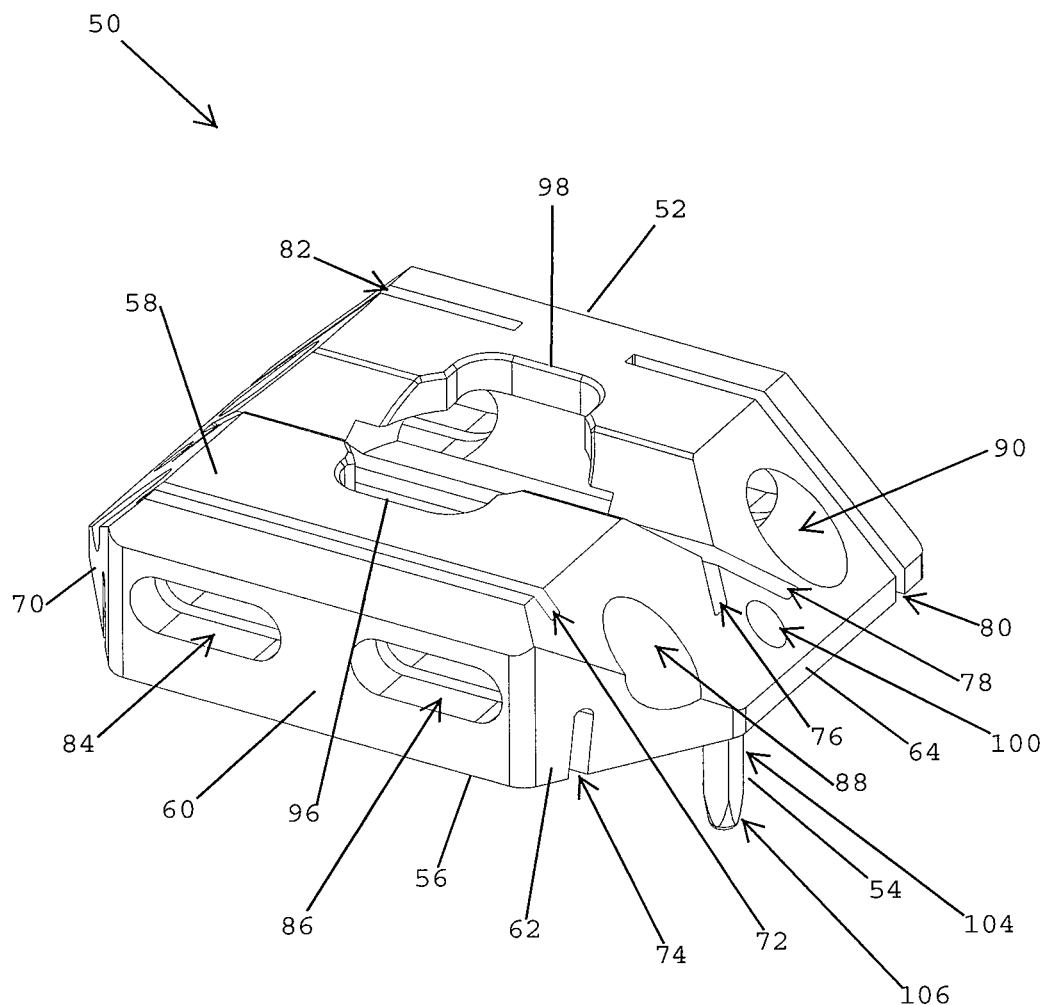
FIG. 7 is an isometric view of a femoral cut block assembly.
Figure 8:
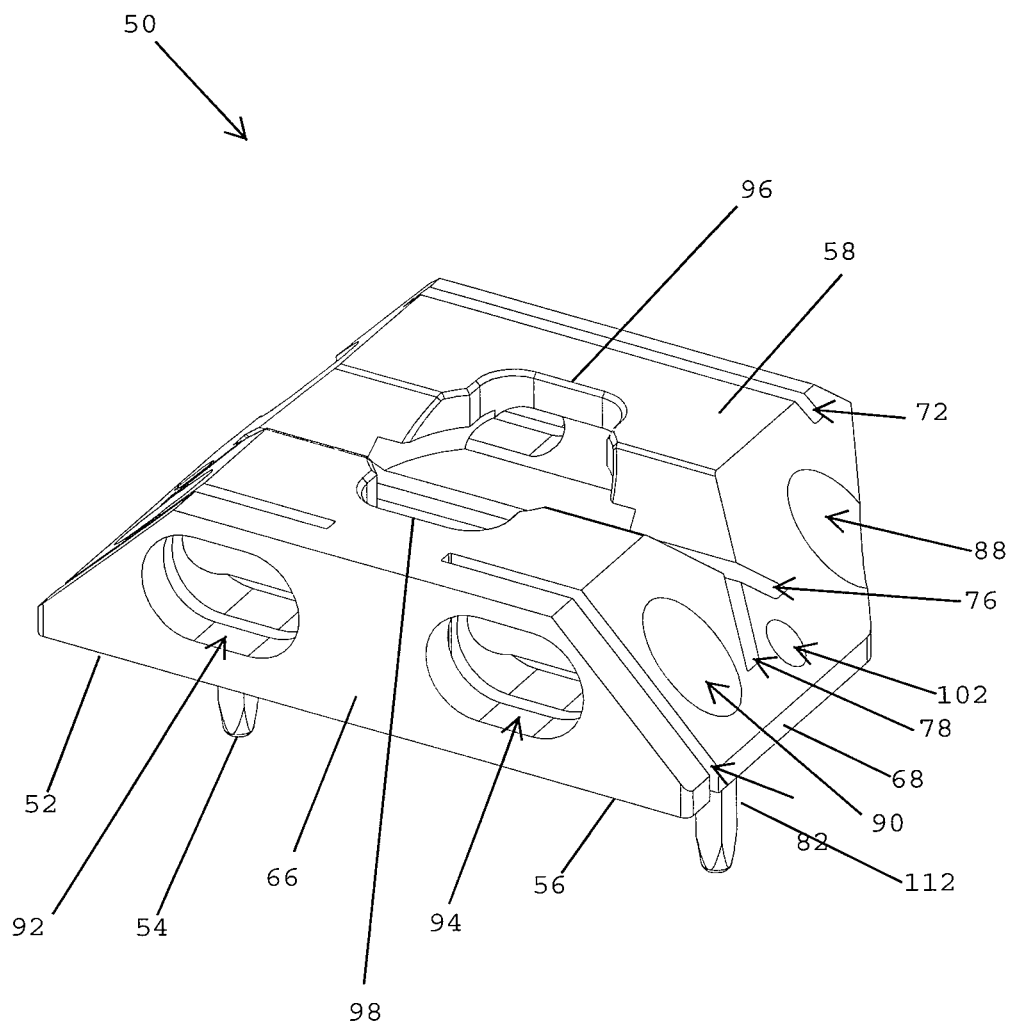
FIG. 8 is another isometric view of the femoral cut block assembly of FIG. 7.
Figure 9:
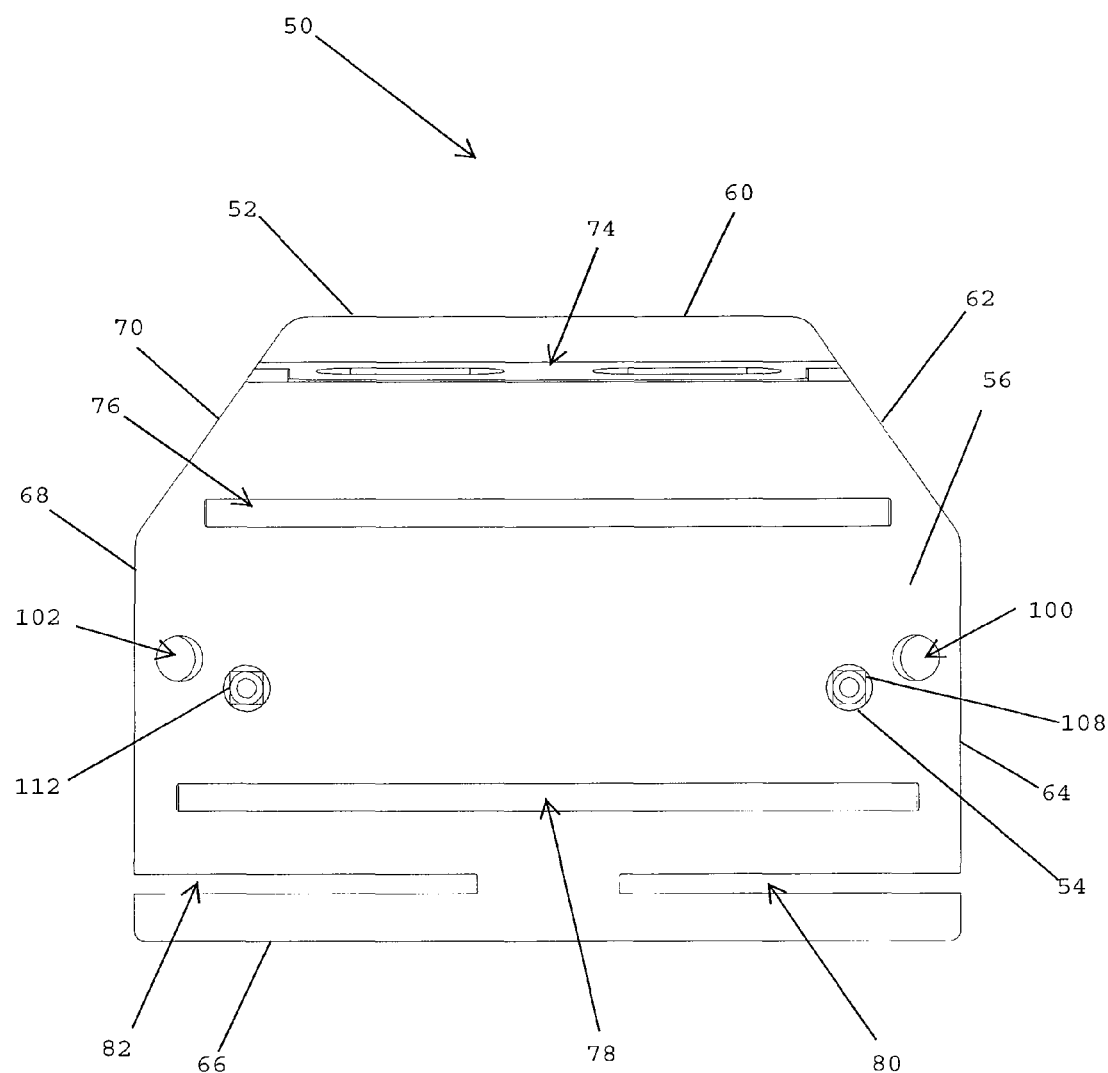
FIG. 9 is a superior view of the femoral cut block assembly of FIG. 7.
Figure 10:
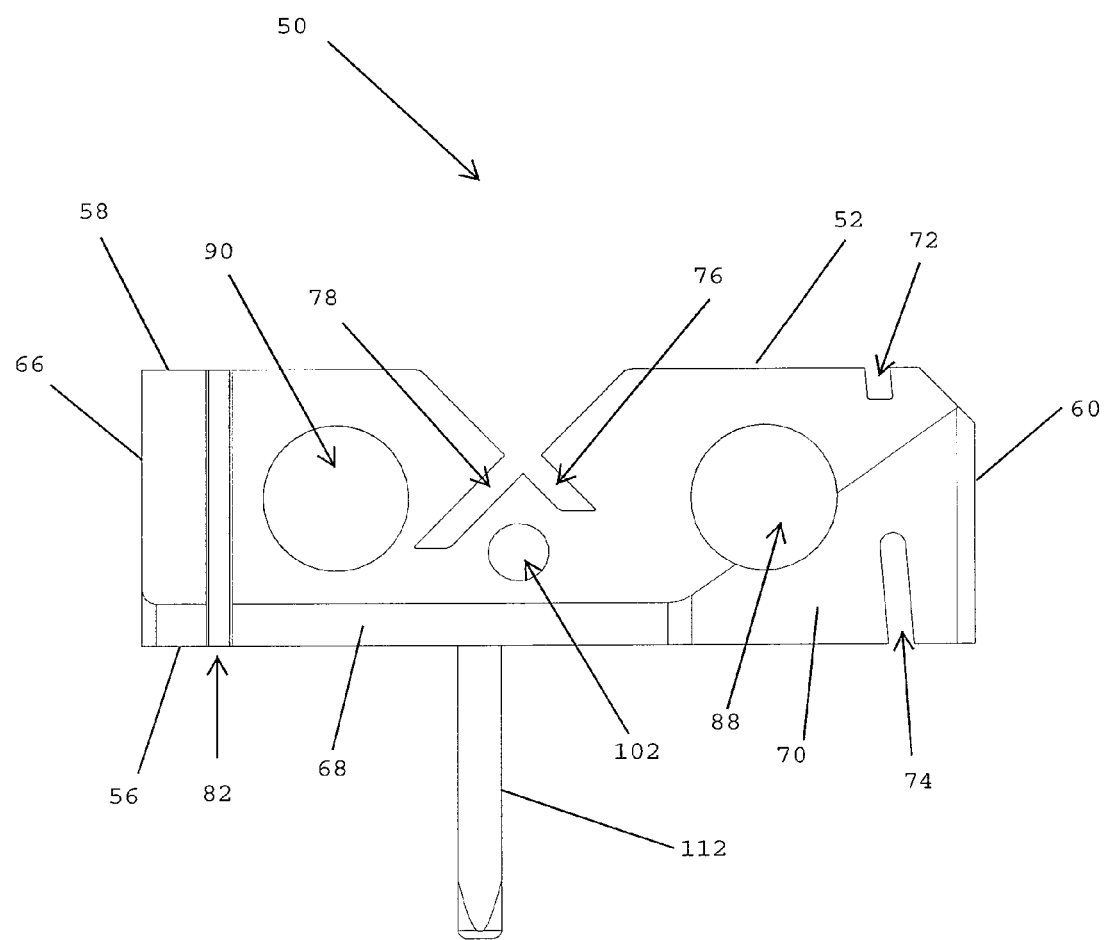
FIG. 10 is a side view of the femoral cut block assembly of FIG. 7.
Figure 11:
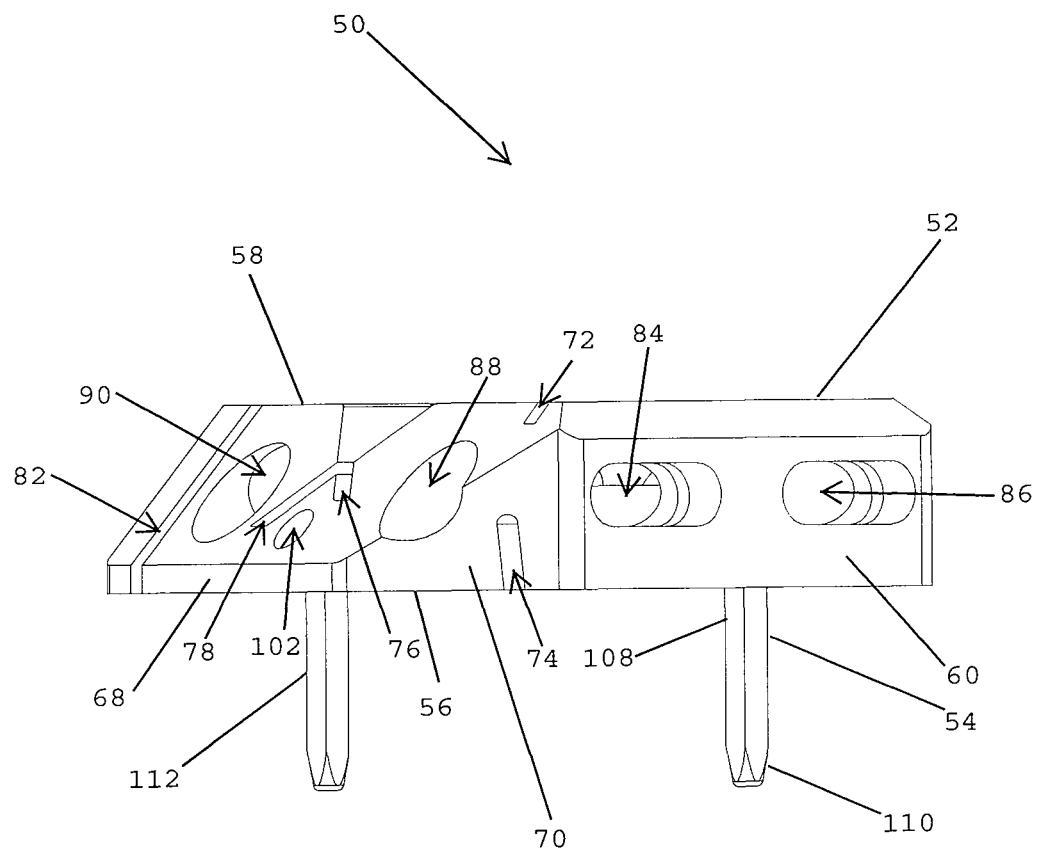
FIG. 11 is an oblique view of the femoral cut block assembly of FIG. 7.
Figure 12:
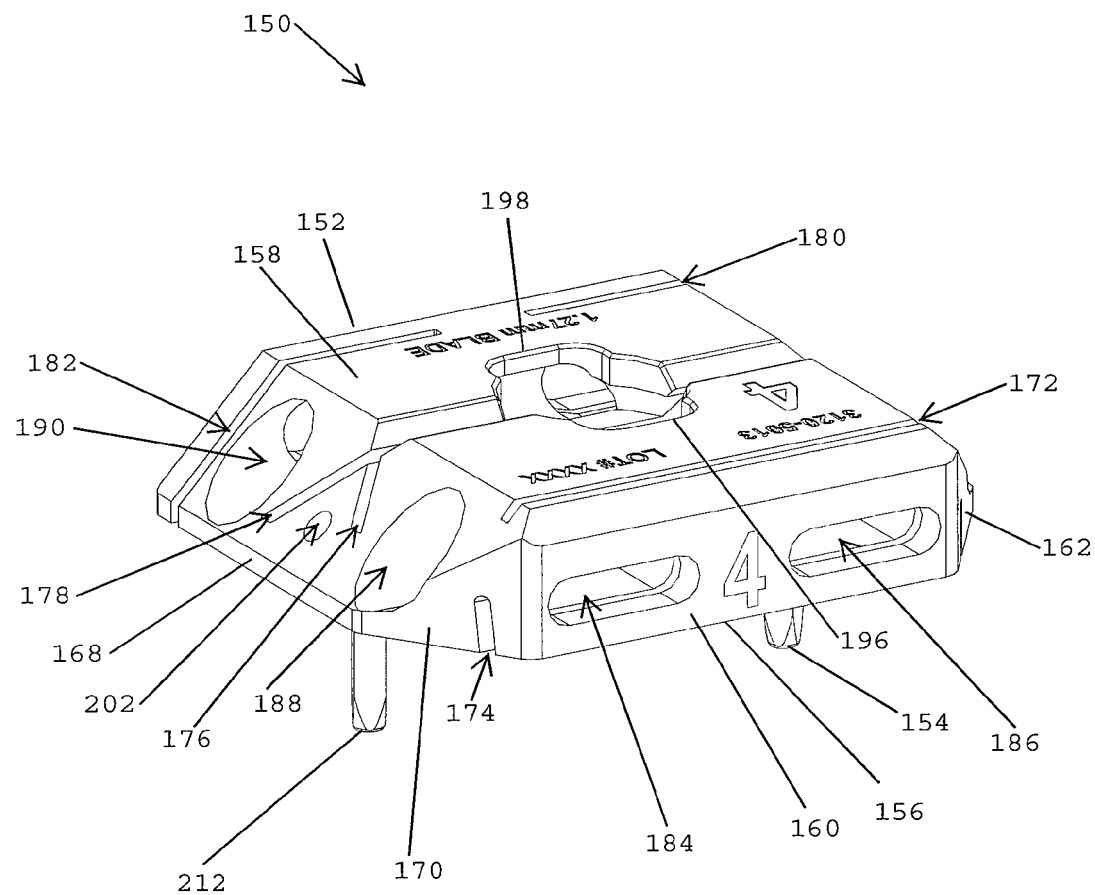
FIG. 12 is an isometric view of another femoral cut block assembly.
Figure 13:
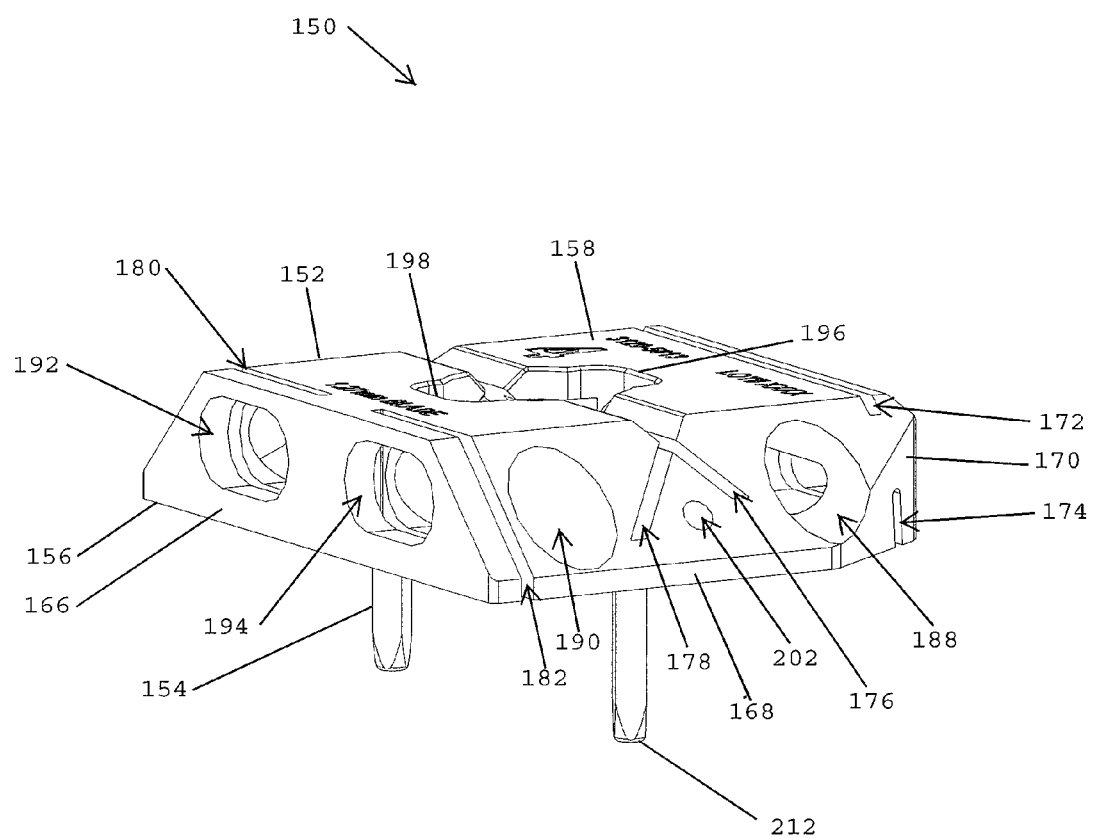
FIG. 13 is another isometric view of the femoral cut block assembly of FIG. 12.
Figure 14:
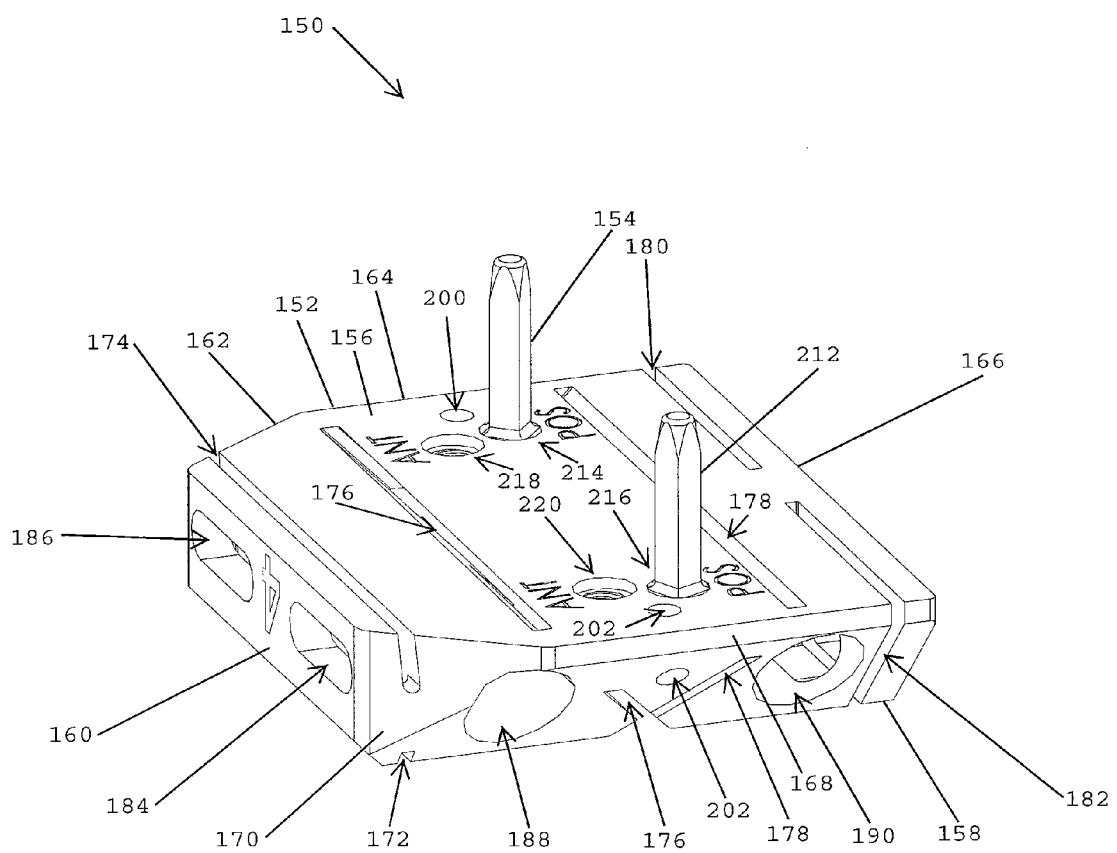
FIG. 14 is another isometric view of the femoral cut block assembly of FIG. 12.

Referring primarily to FIGS. 2 and 6, the anterior fin 36 may project anteriorly from the post portion 14, and may project in line with the central anterior-posterior rib 25. The anterior fin 36 may extend along the full length of the post portion 14 as shown in the illustrated example, or just a portion of the length. For example, the anterior fin 36 may extend along only the proximal 30 portion of the post portion 14. The anterior fin 36 may include a chamfer 44 or taper which reduces the height of the anterior fin 36 as the anterior fin progresses from proximal to distal along the post portion 14. In the example shown, the chamfer 44 extends along a portion of the fin 36. However, the chamfer 44 may extend the full length of the fin 36 in other examples. A straight chamfer is shown, but convex or concave chamfers are contemplated. The chamfered fin 36 occupies less volume than would a non-chamfered or straight full-height fin. The chamfer design reduces volume in the distal portion 32 of the post portion 14, which is the leading end of the post portion 14 during insertion of the post portion into a prepared proximal tibia. Therefore, less bone removal is required where the tibia naturally tapers to the diaphysis.

Referring primarily to FIGS. 2 and 4, the right fin 38 may project obliquely postero-laterally from the post portion 14, and may project in line with the oblique ribs 27. The right fin 38 may extend along the full length of the post portion 14 as shown in the illustrated example, or just a portion of the length. For example, the right fin 38 may extend along only the proximal 30 portion of the post portion 14. The right fin 38 may include a chamfer 46 or taper which reduces the height of the right fin 38 as the right fin progresses from proximal to distal along the post portion 14. In the example shown, the chamfer 46 extends along a portion of the fin 38. However, the chamfer 46 may extend the full length of the fin 38 in other examples. A concave chamfer is shown, but convex or straight chamfers are contemplated. The chamfered fin 38 occupies less volume than would a non-chamfered or straight full-height fin. The chamfer design reduces volume in the distal portion 32 of the post portion 14, which is the leading end of the post portion 14 during insertion of the post portion into a prepared proximal tibia. Therefore, less bone removal is required where the tibia naturally tapers to the diaphysis. The left fin 40 may be a mirror image of the right fin 38.

Referring primarily to FIGS. 4 and 6, the posterior fin 42 may project posteriorly from the post portion 14, and may project in line with the central anterior-posterior rib 25. The posterior fin 42 may extend along the full length of the post portion 14 as shown in the illustrated example, or just a portion of the length. For example, the posterior fin 42 may extend along only the proximal 30 portion of the post portion 14. The posterior fin 42 may include a chamfer 48 or taper which reduces the height of the posterior fin 42 as the posterior fin progresses from proximal to distal along the post portion 14. In the example shown, the chamfer 48 extends along a portion of the fin 42. However, the chamfer 48 may extend the full length of the fin 42 in other examples. A straight chamfer is shown, but convex or concave chamfers are contemplated. The chamfered fin 42 occupies less volume than would a non-chamfered or straight full-height fin. The chamfer design reduces volume in the distal portion 32 of the post portion 14, which is the leading end of the post portion 14 during insertion of the post portion into a prepared proximal tibia. Therefore, less bone removal is required where the tibia naturally tapers to the diaphysis.

Referring to FIGS. 7-11, a cut block assembly 50 includes a cut block 52 and at least one pin 54. The cut block assembly 50 may be used during a total knee arthroplasty procedure to guide saw cuts to the distal femur.

The cut block 52 may include a superior side 56, an inferior side 58, and at least one lateral side 60. The illustrated example includes six lateral sides 60, 62, 64, 66, 68, 70. Lateral side 62 may be referred to as a chamfer, as it forms oblique angles with adjacent lateral sides 60 and 64. Likewise, lateral side 70 may be referred to as a chamfer, as it forms oblique angles with adjacent lateral sides 60 and 68. The cut block 52 may also include one or more slots 72. The illustrated example includes six slots 72, 74, 76, 78, 80, 82. Slot 74 may intersect slot 72 to form a passageway through the cut block 52 between the superior side 56 and the inferior side 58. Slot 76 may intersect slot 78. The cut block 52 may also include one or more apertures 84. The illustrated example includes eight apertures 84, 86, 88, 90, 92, 94, 100, 102. Apertures 84 and 86 intersect aperture 88 and extend no farther. Similarly, apertures 92 and 94 intersect aperture 90 and extend no farther. The cut block 52 may also include one or more alcoves 96. The illustrated example includes two alcoves 96, 98. Alcove 96 intersects aperture 88 and extends no farther. Alcove 98 intersects aperture 90 and extends no farther.

A proximal portion 104 of the pin 54 may couple or mount to the cut block 52, such as by integral formation, press fit, threads, latching, spring detents, magnetic detents, or the like. A distal portion 106 of the pin 54 may extend away from the cut block 52, and may terminate in a free-end. The proximal portion 104 of the pin 54 may include an anti-rotation portion 108 with a square or rectangular cross section, as may be appreciated in FIGS. 7 and 9. The portion 108 may alternatively have a triangular or hexagonal shape, or another shape that resists rotation. The distal portion 106 of the pin 54 may include a tapered portion 110, as may be appreciated in FIGS. 7 and 11, so that the free end has a smaller diameter than the proximal portion 104 of the pin. In the example shown, the tapered portion is conical, although pyramidal tapered portions are contemplated. The tapered portion 110 may extend along a portion of the length of the pin 54, or may extend along the entire length of the pin. The example shown includes a second pin 112, which may be identical to pin 54.

In use, the cut block assembly 50 may be used early in the preparation of a distal femur. For the example shown, two holes may be drilled into the distal femur, one in the distal aspect of each condyle. A drill guide or jig may be used to align, orient, and position the holes relative to anatomical landmarks on the femur and/or to each other. The free ends of the pins 54, 112 may be inserted into the holes, and the pins advanced until the superior side 56 contacts the distal aspect of the femur. As the pins 54, 112 advance within the holes, the fit of the pins becomes tighter and tighter along the tapered portion 110. As the square portions 108 (or other rotation-resisting shape) enter the holes, the corners of the squares have an interference fit with the holes. The corners may gradually cut into the bone or force the bone out of the way. The square pegs in the round holes, with an interference fit, provides secure fixation of the cut block assembly 50 in the host bone.

The cut block assembly 50 may thus be described as a four in one cut block assembly 150. The four in one designation refers to the slots 72, 74, 76, 78, 80, 82 which may guide a cutting tool, such as a saw blade, to make anterior, posterior, and two chamfer cuts in the distal femur with one cut block, without repositioning the cut block.

Referring to FIGS. 12-17, another cut block assembly 150 includes a cut block 152 and at least one pin 154. The cut block assembly 150 may be used during a total knee arthroplasty procedure to guide saw cuts to the distal femur.

The cut block 152 may include a superior side 156, an inferior side 158, and at least one lateral side 160. The illustrated example includes six lateral sides 160, 162, 164, 166, 168, 170. Lateral side 162 may be referred to as a chamfer, as it forms oblique angles with adjacent lateral sides 160 and 164. Likewise, lateral side 170 may be referred to as a chamfer, as it forms oblique angles with adjacent lateral sides 160 and 168. The cut block 152 may also include one or more slots 172. The illustrated example includes six slots 172, 174, 176, 178, 180, 182. Slot 174 may intersect slot 172 to form a passageway through the cut block 152 between the superior side 156 and the inferior side 158. Slot 176 may intersect slot 178. The cut block 152 may also include one or more apertures 184. The illustrated example includes eight apertures 184, 186, 188, 190, 192, 194, 200, 202. Apertures 184 and 186 intersect aperture 188 and extend no farther. Similarly, apertures 192 and 194 intersect aperture 190 and extend no farther. The cut block 152 may also include one or more alcoves 196. The illustrated example includes two alcoves 196, 198. Alcove 196 intersects aperture 188 and extends no farther. Alcove 198 intersects aperture 190 and extends no farther.

The cut block 152 may include at least one pin mounting location, such as hole 214 that receives at least a portion of the pin 154. In the example shown, four holes 214, 216, 218, 220 are provided, although any number of holes may be present in other examples. The hole(s) may include internal threads or other connection features or retention means for coupling to the pin 154. The hole(s) may alternatively be made with a clearance fit, line to line fit, or interference fit with the pin 154. Any hole may receive any pin. Other mounting locations may include internal or external features. The cut block 152 may include indicia, markings, or labels to indicate the use of the holes 214, 216, 218, 220. In the example shown, the cut block 152 includes markings "POS" adjacent to holes 214, 216, indicating that these holes are located for use with posterior referencing, as discussed below. The cut block 152 includes markings "ANT" adjacent to holes 218, 220, indicating that these holes are located for use with anterior referencing. Holes 218, 220 are also closer together than holes 214, 216 to reduce the likelihood that a user will erroneously use the "ANT" holes 218, 220 in the cut block 152 with posterior referencing, or vice versa.

A proximal portion 204 of the pin 154 may couple to the cut block 152, such as by integral formation, press fit, threads, latching, spring detents, magnetic detents, or the like. A distal portion 206 of the pin 154 may extend away from the cut block 152, and may terminate in a free end. The proximal portion 204 of the pin 154 may include an anti-rotation portion 208 with a square or rectangular cross section, as may be appreciated in FIG. 15. The portion 208 may alternatively have a triangular or hexagonal shape, or another shape that resists rotation. The distal portion 206 of the pin 154 may include a tapered portion 210, as may be appreciated in FIG. 16, so that the free end has a smaller diameter than the proximal portion 204 of the pin. In the example shown, the tapered portion is conical, although pyramidal tapered portions are contemplated. The tapered portion 210 may extend along a portion of the length of the pin 154, or may extend along the entire length of the pin. The example shown includes a second pin 212, which may be identical to pin 154. Pins 54, 154, 112, 212 may all be identical and interchangeable between cut blocks 52, 152.

Figure 15:
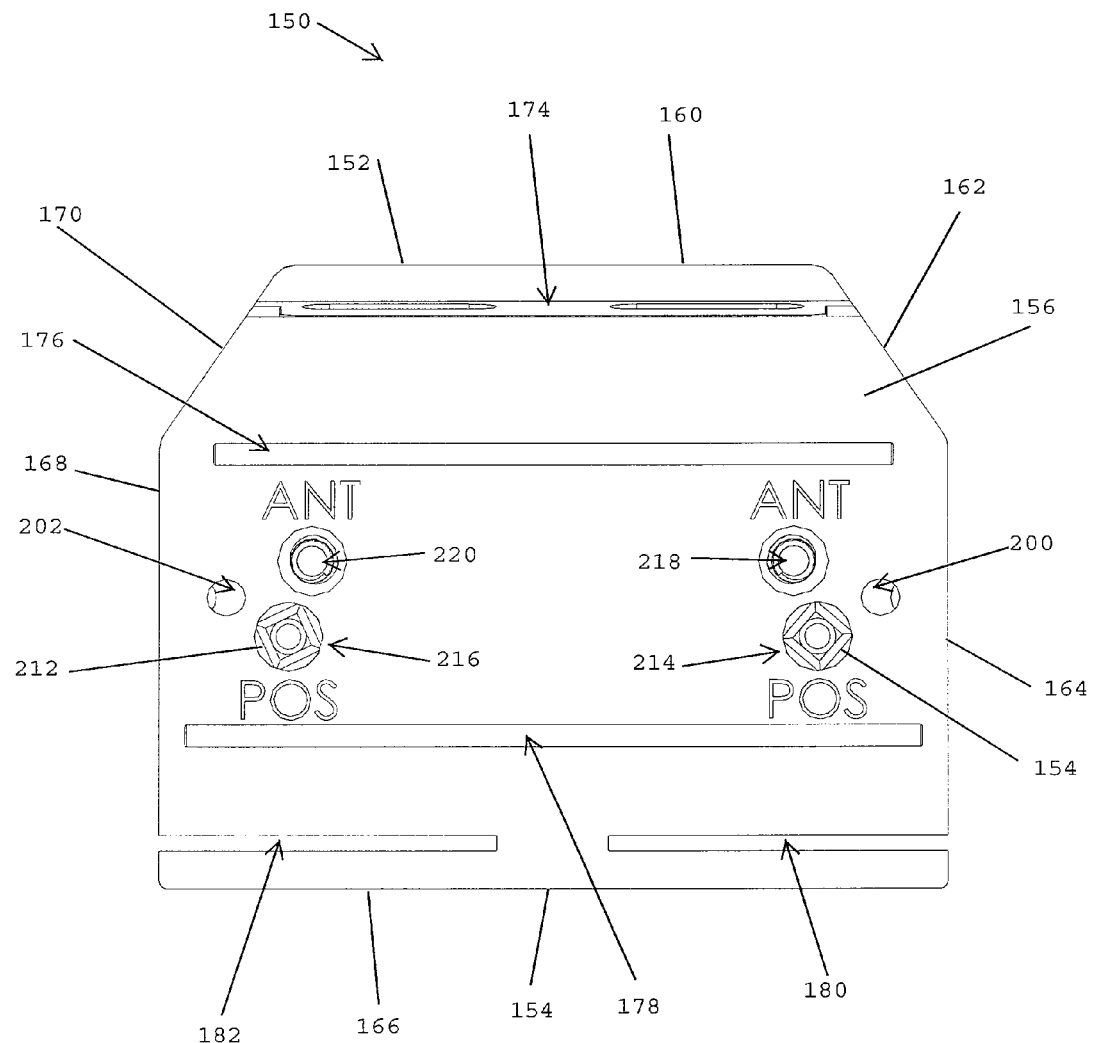
FIG. 15 is a superior view of the femoral cut block assembly of FIG. 12.
Figure 16:
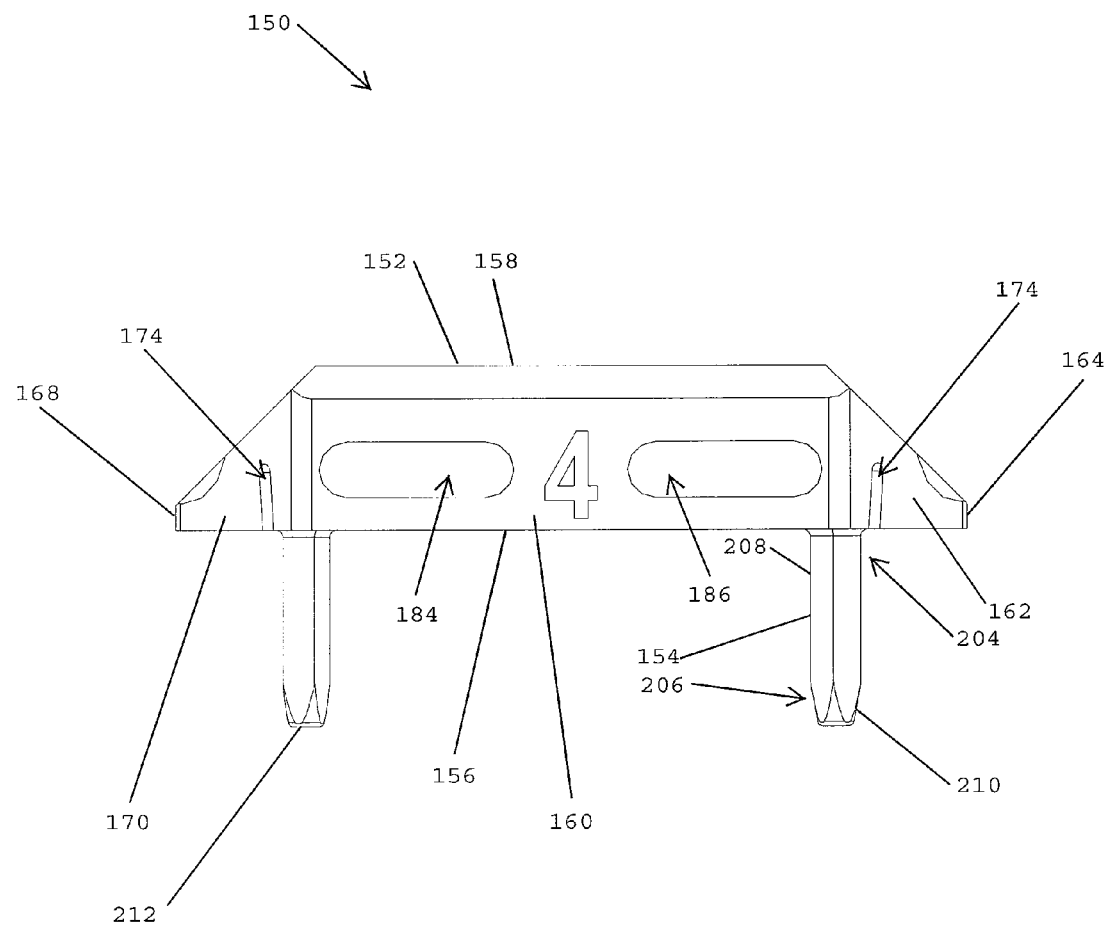
FIG. 16 is a side view of the femoral cut block assembly of FIG. 12.
Figure 17:
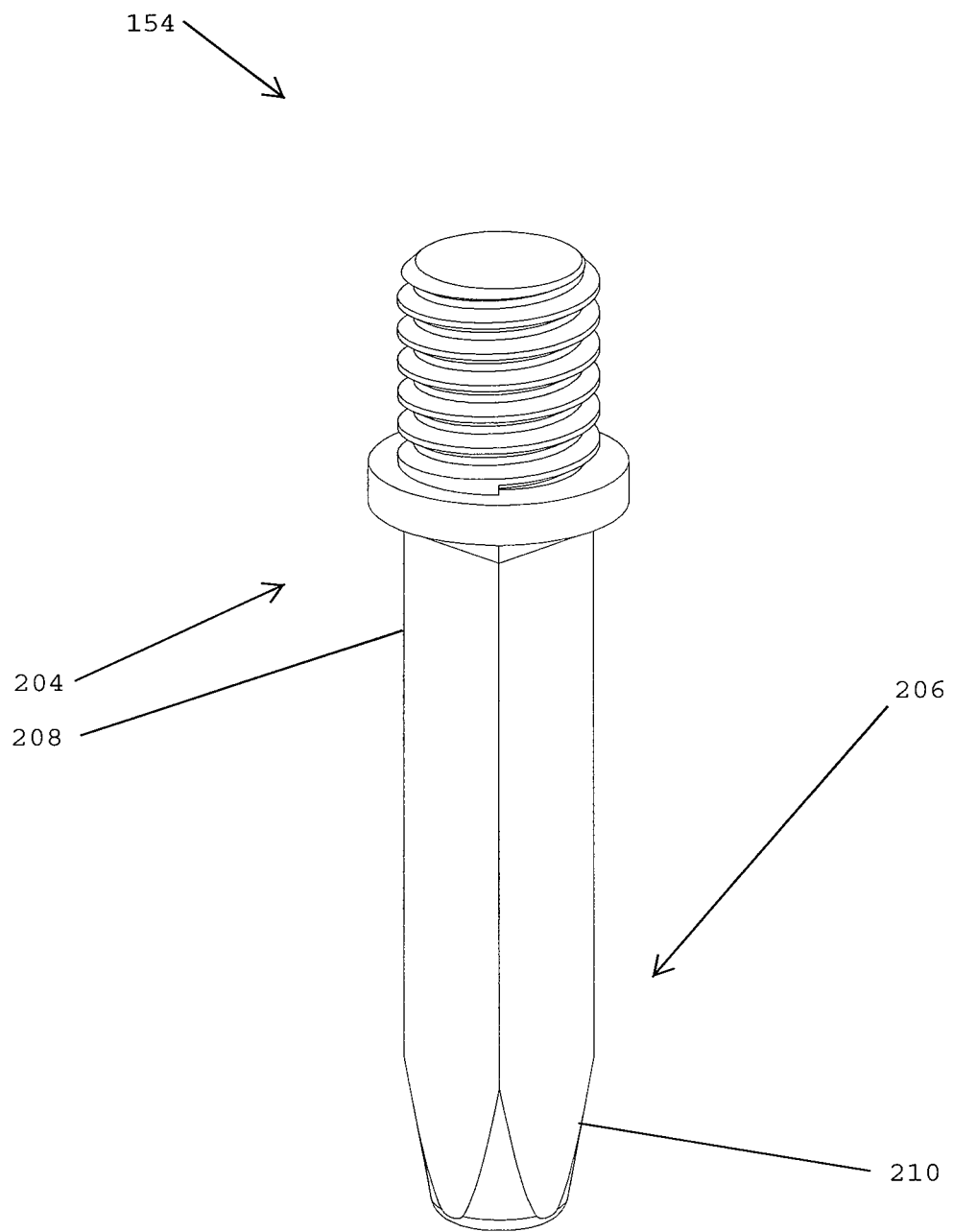
FIG. 17 is an isometric view of a pin for use in a femoral cut block assembly.

In use, the cut block assembly 150 may be used early in the preparation of a distal femur. For the example shown, two holes may be drilled into the distal femur, one in the distal aspect of each condyle. A drill guide or jig may be used to align, orient, and position the holes relative to anatomical landmarks on the femur and/or to each other. The location of the holes may be determined based on referencing the anterior portion or the posterior portion of the distal femur. When the holes are located based on anterior referencing, the pins 152, 212 may be secured in holes 218, 220, which are labeled "ANT" (FIG. 15). When the holes are located based on posterior referencing, the pins 152, 212 may be secured in holes 214, 216, which are labeled "POS" (FIG. 15). The free ends of the pins 154, 212 may be inserted into the holes, and the pins advanced until the superior side 156 contacts the distal aspect of the femur. As the pins 154, 212 advance within the holes, the fit of the pins becomes tighter and tighter along the tapered portion 210. As the square portions 208 (or other rotation-resisting shape) enter the holes, the corners of the squares have an interference fit with the holes. The corners may gradually cut into the bone or force the bone out of the way. The square pegs in the round holes, with an interference fit, provides secure fixation of the cut block assembly 150 in the host bone.

The cut block assembly 150 may thus be described as a two position four in one cut block assembly 150. The two position designation refers to the "ANT" and "POS" positions for the pins. The four in one designation refers to the slots 172, 174, 176, 178, 180, 182 which may guide a cutting tool, such as a saw blade, to make anterior, posterior, and two chamfer cuts in the distal femur with one cut block, without repositioning the cut block.

The components disclosed herein may be fabricated from metals, alloys, polymers, plastics, ceramics, glasses, composite materials, or combinations thereof, including but not limited to: PEEK, titanium, titanium alloys, commercially pure titanium grade 2, ASTM F67, Nitinol, cobalt chrome, stainless steel, ultra high molecular weight polyethylene (UHMWPE), biocompatible materials, and biodegradable materials, among others. Different materials may be used for different parts. Different materials may be used within a single part. Any component disclosed herein may be colored, coded or otherwise marked to make it easier for a user to identify the type and size of the component, the setting, the function(s) of the component, and the like.

It should be understood that the present systems, kits, apparatuses, and methods are not intended to be limited to the particular forms disclosed. Rather, they are to cover all combinations, modifications, equivalents, and alternatives falling within the scope of the claims.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

In the foregoing Detailed Description, various features are grouped together in several examples for the purpose of streamlining the disclosure. This method of disclosure is not to be interpreted as reflecting an intention that the examples of the invention require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example.

The invention claimed is:

1. A knee prosthesis comprising:
   a tibial tray having a superior surface and an inferior surface with a peripheral wall therebetween defining an anterior side and a posterior side;
   a peripheral rib extending from the anterior side to the posterior side forming a peripheral around the tibial tray;
   at least one rib located on said inferior surface positioned along an area that experiences service stress during at least a portion of a gait cycle when the tibia tray is operatively mounted to a prepared proximal tibia;
   a post having a proximal end intersecting at least one said rib on said inferior surface and extending to a distal end;
   at least one fin projecting anteriorly when the tibial tray is operatively mounted to a prepared proximal tibia and radially from a longitudinal axis of the post;
   a cut block for proper positioning of said knee prosthesis, said cut block is substantially rectangular having a cut block superior side and a cut block inferior side with six lateral sides therebetween;
   at least four slots forming a passageway from the cut block superior side to the cut block inferior side, a first slot to allow an anterior cut, a second slot to allow a posterior cut, a third slot to allow a first chamber cut, and a fourth slot to allow a second chamber cut; and
   a pin having a proximal portion attached to said cut block inferior side and a distal portion extending outward and terminating in a free end;
   wherein said cut block is used to prepare a distal femur for receipt of said knee prosthesis, each said slot may be used as a guide for a cutting tool.

2. The knee prosthesis according to claim 1 wherein at least one said rib extends across inferior surface from the anterior side to the posterior side of the tibial tray to coincide with the direction of knee flexion and extension motion.

3. The knee prosthesis according to claim 1 wherein at least one rib includes a radiused or filleted edge to lessen stress concentrations.

4. The knee prosthesis according to claim 1 wherein said post includes an anterior fin, a right fin, a left fin, and a posterior fin.

5. The knee prosthesis according to claim 4 wherein said posterior fin projects in line with a central anterior-posterior rib.

6. The knee prosthesis according to claim 4 wherein said posterior fin includes a chamfer to reduce the height of the fin as it progresses from said proximal end to said distal end.

7. The knee prosthesis according to claim 4 wherein said superior surface is convex.

8. The knee prosthesis according to claim 1 wherein said superior surface is concave.

9. The cut block according to claim 1 wherein said superior side of said cut block includes at least one alcove.

10. The cut block according to claim 1 wherein said pin is shaped to resist rotation when inserted into bone.

11. The cut block according to claim 10 wherein said pin shape is selected from the group of square, rectangular, triangular or a hexagonal shape.

12. The cut block according, to claim 1 wherein said inferior surface includes a plurality of mounting locations for coupling said pin to the cut block.

* * * * *